(12) United States Patent
Zanella et al.

(10) Patent No.: US 9,230,318 B2
(45) Date of Patent: Jan. 5, 2016

(54) ANALYSIS OF THE DIGITAL IMAGE OF THE EXTERNAL SURFACE OF A TYRE AND PROCESSING OF FALSE MEASUREMENT POINTS

(75) Inventors: Jean-Paul Zanella, Clermont-Ferrand (FR); Claire Moreau, Clermont-Ferrand (FR); Guillaume Noyel, Clermont-Ferrand (FR); Yusi Shen, Clermont-Ferrand (FR)

(73) Assignees: COMPAGNIE GENERALE DES ETABLISSEMENTS MICHELIN, Clermont-Ferrand (FR); MICHELIN RECHERCHE ET TECHNIQUE S.A., Granges-Paccot (CH)

( * ) Notice: Subject to any disclaimer, the term of this patent is extended or adjusted under 35 U.S.C. 154(b) by 0 days.

(21) Appl. No.: 14/112,448

(22) PCT Filed: Mar. 21, 2012

(86) PCT No.: PCT/EP2012/055016
§ 371 (c)(1),
(2), (4) Date: Mar. 12, 2014

(87) PCT Pub. No.: WO2012/143198
PCT Pub. Date: Oct. 26, 2012

(65) Prior Publication Data
US 2014/0307941 A1    Oct. 16, 2014

(30) Foreign Application Priority Data

Apr. 18, 2011 (FR) ...................................... 11 53345

(51) Int. Cl.
*G06K 9/00* (2006.01)
*G06T 7/00* (2006.01)
(Continued)

(52) U.S. Cl.
CPC ............. *G06T 7/001* (2013.01); *G01M 17/027* (2013.01); *G06T 3/0056* (2013.01); *G06T 5/002* (2013.01);
(Continued)

(58) Field of Classification Search
CPC .................................. G06T 7/001; G06T 5/30
See application file for complete search history.

(56) References Cited

U.S. PATENT DOCUMENTS

| 4,951,676 A | 8/1990 | Collet-Billon ........... 128/660.01 |
| 2001/0013823 A1 | 8/2001 | Hatakeyama et al. ......... 340/3.1 |

(Continued)

FOREIGN PATENT DOCUMENTS

| EP | 0 345 852 A1 | 12/1989 |
| WO | WO 03/023699 A1 | 3/2003 |

OTHER PUBLICATIONS

Z. Tauber et al., "Review and Preview Disocclusion by Inpainting for Image-Based Rendering," IEEE Transactions on Systems, Man, and Cybernetics: Part C: Applications and Reviews, vol. 37, No. 4, pp. 527-540 (2007).

(Continued)

*Primary Examiner* — Samir Ahmed
(74) *Attorney, Agent, or Firm* — Fitzpatrick, Cella, Harper & Scinto

(57) ABSTRACT

A method for processing an image of a surface of a tire to be inspected is described. A three-dimensional digital image is captured of the surface, and each pixel of a plane of the image is assigned an item of information relating to an elevation of the pixel with respect to the surface. By utilizing of a morphological operator that uses a structuring element, a first transformation of the image of the surface is performed with aid of an opening and then of a closing, so as to tailor a grey level of pixels situated abnormally above or below the surface.

12 Claims, 3 Drawing Sheets

(51) Int. Cl.
  *G01M 17/02* (2006.01)
  *G06T 3/00* (2006.01)
  *G06T 5/00* (2006.01)
  *G06T 5/30* (2006.01)
  *G01N 21/952* (2006.01)

(52) U.S. Cl.
  CPC ............. *G06T 5/30* (2013.01); *G01N 21/952* (2013.01); *G06T 2207/10028* (2013.01); *G06T 2207/20036* (2013.01); *G06T 2207/30108* (2013.01); *G06T 2207/30164* (2013.01)

(56) References Cited

U.S. PATENT DOCUMENTS

| | | | |
|---|---|---|---|
| 2003/0012453 A1 | 1/2003 | Kotlikov et al. | 382/275 |
| 2004/0071334 A1 | 4/2004 | Hassler et al. | 382/141 |
| 2005/0259859 A1 | 11/2005 | Hassler et al. | 382/141 |
| 2007/0209431 A1* | 9/2007 | Fujisawa et al. | 73/146 |
| 2008/0218742 A1* | 9/2008 | Sakoda et al. | 356/73 |
| 2008/0319706 A1 | 12/2008 | Uffenkamp et al. | 702/150 |
| 2011/0013823 A1 | 1/2011 | Joly | 382/141 |
| 2011/0018999 A1* | 1/2011 | Joly et al. | 348/148 |
| 2011/0019903 A1* | 1/2011 | Joly et al. | 382/141 |
| 2011/0069323 A1* | 3/2011 | Takahashi et al. | 356/625 |
| 2013/0202156 A1 | 8/2013 | Joly et al. | 283/104 |
| 2013/0208949 A1 | 8/2013 | Joly et al. | 382/103 |

OTHER PUBLICATIONS

J. Davis et al., "Filling Holes in Complex Surfaces using Volumetric Diffusion," Proceedings of the First International Symposium on 3D Data Processing Visualization and Transmission, 15 pages (2002).

J. Oh et al., "Ranked Directional Morphological Filtering of Impulse Noise in Images," Proceedings of the IEEE International Conference on Acoustics, Speech, and Signal Processing, vol. 6, pp. 2167-2170 (2000).

R. A. Peters, "A New Algorithm for Image Noise Reduction Using Mathematical Morphology," IEEE Transactions on Image Processing, vol. 4, No. 5, pp. 554-568 (1995).

P. Salembier et al., "Hierarchical Morphological Segmentation for Image Sequence Coding," IEEE Transactions on Image Processing, vol. 3, No. 5, pp. 639-651 (1994).

Li Jie, "Detecting Tire Tread Morphology Based on Laser Triangulation," Master's Thesis (full document), Changchun University of Science and Technology (Feb. 15, 2010).

Dong Jiyang et al., "A Simple Algorithm for Removing Salt and Pepper Noise from Gray-scale Image," Computer Engineering and Applications, vol. 20, pp. 27-29 (2003).

* cited by examiner

the image capture means,

ANALYSIS OF THE DIGITAL IMAGE OF THE EXTERNAL SURFACE OF A TYRE AND PROCESSING OF FALSE MEASUREMENT POINTS

FIELD OF THE INVENTION

The invention relates to the field of tyre manufacture and more particularly the field of automatic inspection of the surface of a tyre with a view to establishing a diagnosis of compliance with pre-established references.

RELATED ART

One of the steps of this process consists, in a known manner, in acquiring the three-dimensional image of the surface of the tyre.

The acquisition of this image is carried out with the aid of means based on the principle of optical triangulation, using for example a 2D sensor coupled with a light source of the laser type.

The topographical image of the tyre surface is in fact a two-dimensional image, called a grey-level image, in which, with every point, i.e. with every pixel (x, y) of the image, is associated a value f(x, y), called grey level, and usually between 0 and 255.

This value of grey level may usefully be encoded on 8 or 16 bits for a better dynamic. The grey level represents the altitude of this point relative to the surface. For encoding on 8 bits, the value 255 (white) corresponds to the highest altitude, and the value 0 (black) corresponds to the lowest altitude. As a general rule, the pixels of the image are placed in lines and in columns.

It is however observed that the image of the surface originating from these acquisition means may have false-measurement points which it is necessary to identify and to cause to disappear before undertaking the subsequent digital processes. Otherwise, the analysis algorithms could incorrectly consider these zones to be structural anomalies of the tyre to be inspected.

These points appear as a general rule in the zones exhibiting a variation in significant relief because of the angle of incidence of the light on the surface of the tyre to be inspected. The camera incorrectly records the information originating from the reflected light instead of considering the information originating from the incident beam. This situation arises as a general rule when considering the external surface of the tyre notably at the periphery of the tread blocks.

All these points, called false-measurement points, are distinguished by the fact that they have positions that are extremely offset relative to the points situated in their immediate environment. Extremely offset positively (bump) or negatively (pit) is here intended to mean an offset of greater than 4 or 5 mm, which is therefore sharply distinguished from the variations of profile commonly appearing on the surface of a tyre.

BRIEF DESCRIPTION OF EMBODIMENTS OF THE INVENTION

The object of the invention is to propose a simple processing method making it possible to identify these points, and a method of correcting the digital values describing the surface.

The method for processing the three-dimensional digital image of the external surface of a tyre according to the invention provides for the use of methods for processing an image with the aid of tools of the morphological type.

These methods consist, in a known manner, in modifying the patterns of the image with tools making it possible to erode it or to expand it. In the present case, this amounts to modifying the reliefs of the surface to be inspected.

The morphological operations of erosion or expansion consist, for each point of an image, in searching for the minimum value or the maximum value of grey level of the neighbouring points lying inside a structuring element, of given shape and area, centred on the point to be analysed and defining a neighbourhood of this point. For an erosion, the value at this point then becomes the minimum value and, for an expansion, the value at this point becomes the maximum value. The combination of an erosion followed by an expansion is called an opening, and the combination of an expansion followed by an erosion is called a closure.

The operator of morphological gradient type makes it possible to delimit the zones of strong variation in relief, i.e. the contours. At each point of the image, a grey level value is assigned, equal to the difference between the grey level value obtained after an expansion and the grey level value obtained after erosion.

After having produced the three-dimensional image of the surface of the said tyre in which each pixel of the image contains an item of information relating to the elevation of the corresponding point of the surface to be inspected, the method according to the invention envisages performing a first transformation of the image of the surface with the aid of an opening and then of a closing, so as to recompute the grey level of the pixels situated abnormally above or below the surface to be inspected.

The grey level of each pixel is representative of the elevation of the corresponding point of the surface to be inspected.

Preferably, the morphological operator for performing the opening and the closing is a square. A square whose width lies between 8 and 15 pixels, corresponding to a slightly greater size than the size of the non-measurement zones, will advantageously be chosen.

It is possible to refine the detection and the elimination of the false-measurement points by observing that, in the case of the image of a tyre, the false-measurement points are situated preferably in the zones exhibiting strong variations of relief and therefore situated at the level of the contours.

A second transformation is then performed, after having carried out the first transformation of the image of the surface, in which:

the elements of contours of the relief of the surface are determined by using a morphological operator of gradient type, followed by a thresholding making it possible to extract the contours of the relief, the grey level value equal to the value obtained after the first transformation is assigned to each pixel of the contour.

Preferably the morphological operator used to determine the contours of the relief is a square. A square whose width lies between 8 and 15 pixels will advantageously be chosen.

This method applies in a preferential manner to the inspection of the external surface of the tyre.

BRIEF DESCRIPTION OF THE DRAWINGS

The following description is based on FIGS. 1 to 5 in which.

DETAILED DESCRIPTION OF EMBODIMENTS OF THE INVENTION

Figure 1:
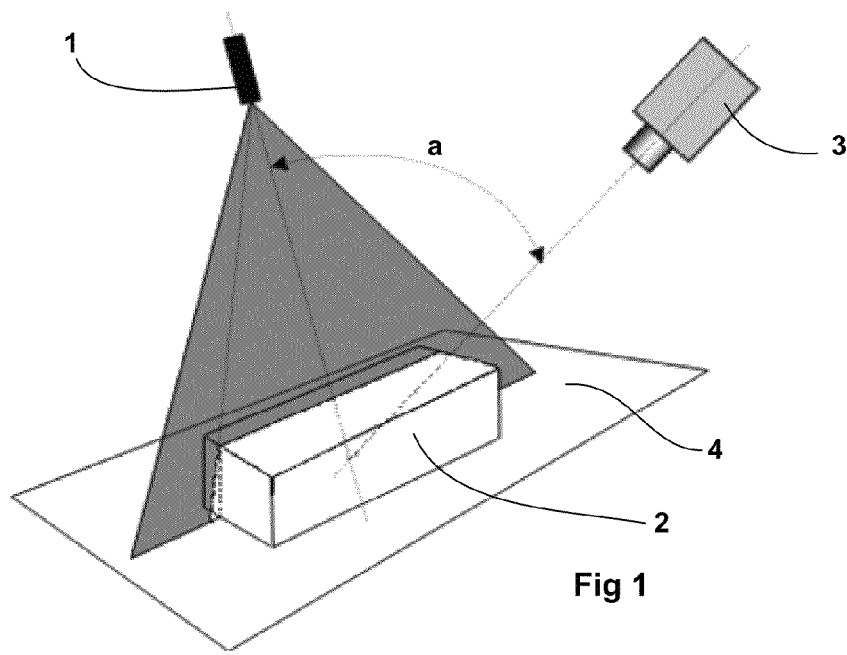
FIG. 1 represents a schematic view of a means for capturing the image of the surface of a tyre.

The acquisition of the image of the surface of a tyre is illustrated in FIG. 1. This acquisition takes place, by way of example, with the aid of a slit light emitted by a laser 1 and of a camera 3 able to capture the 2D image of the illuminated surface. The camera is positioned such that its direction of aim forms a given angle a with the beam emitted by the laser source. By triangulation, it is then possible to determine the coordinates of the element of relief 2 relative to the supporting surface 4. As a general rule, the slit light is directed in an axial or radial direction perpendicularly to the circumferential direction corresponding to the direction of the rotation imposed on the tyre so as to capture a complete image of its surface.

Figure 2:
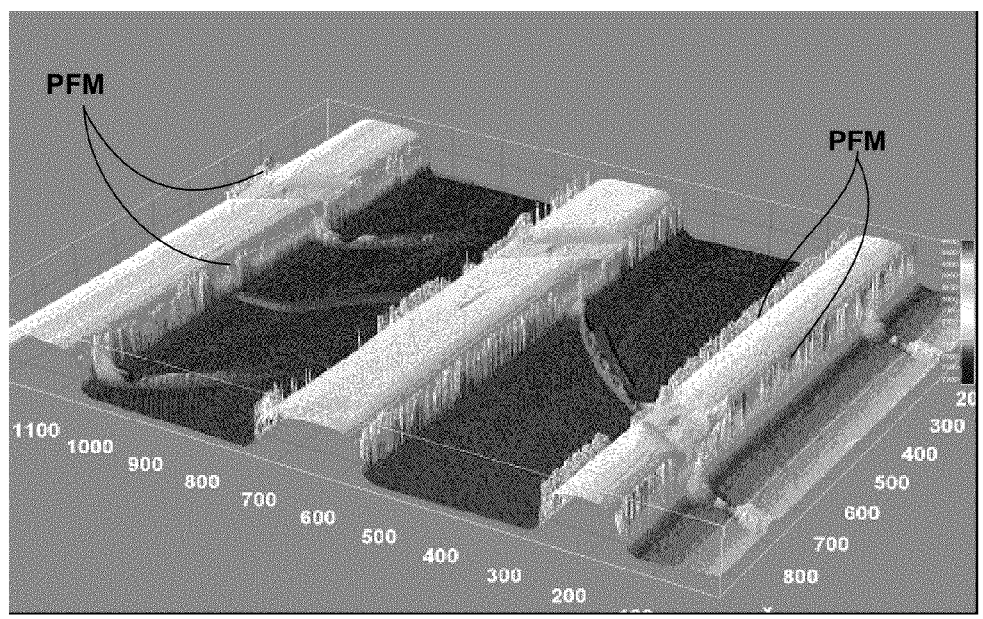
FIG. 2 represents a view of the image of the exterior surface of a tyre arising directly from the image capture means.

FIG. 2 represents the image originating from this capture. The presence is observed of false-measurement points, denoted FMP, whose presence is particularly marked on the edges of the reliefs of the tread.

At each point (x, y) of the supporting plane, a value of grey level is assigned that it is proportional to the elevation of this point relative to the reference surface.

This image is then processed with the aid of the morphological operators of opening and then closing type with the aim of filtering the grey level values that are abnormally high or low with respect to the grey level values assigned to the neighbouring points.

This first processing uses a morphological operator of square shape. The size of this operator is tailored to the size of the defects that it is sought to filter. In this instance, good results are obtained with an operator, the area of whose square is of the order of about a hundred pixels and whose side is about ten pixels wide.

The square is oriented along the axes x and y corresponding respectively, in the case illustrated by FIG. 2, to the axial direction and to the circumferential direction of the tyre.

Figure 3:
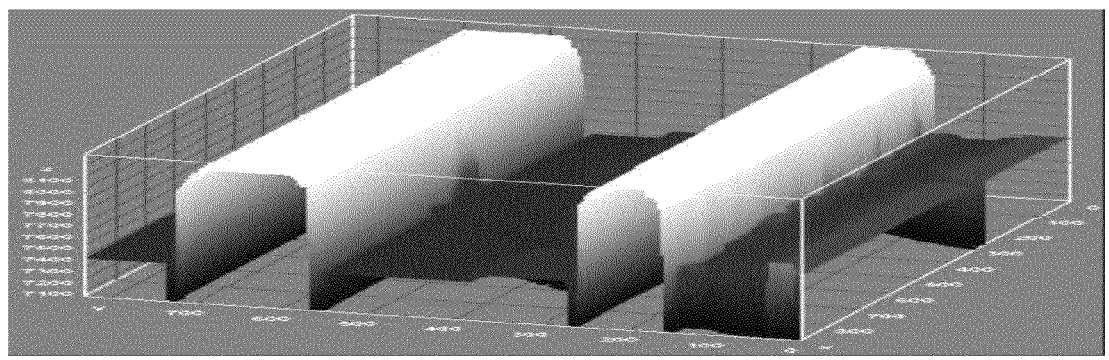
FIG. 3 represents the partial image of the exterior surface after processing with the aid of the first transformation.

FIG. 3 is a partial view of the image of the surface of the tyre after the first process has been carried out.

It is possible that this first processing may not succeed in eliminating all the abnormal values considered to be false-measurement points.

Hence, it will be considered that this residual of abnormal values is concentrated in a preferential manner at the level of the zones corresponding to a strong variation in the relief.

These zones are easily identifiable, because of the strong variation in the grey level gradient, with the aid of a morphological operator of gradient type, which consists in subtracting the grey level values obtained after an erosion of the image arising from the first transformation from the grey level values obtained after an expansion of the said image.

For this operation, use is again made of a morphological operator of square shape whose size is tailored so as to reveal the zone where the strong variation in gradient occurs, and whose width depends on the slope of the relief patterns featuring on the surface of the tyre. As a general rule this slope is relatively significant, in particular at the level of the tread blocks or of the branding patterns featuring on the sidewalls. Here again a square of about a hundred pixels gives good results.

Figure 4:
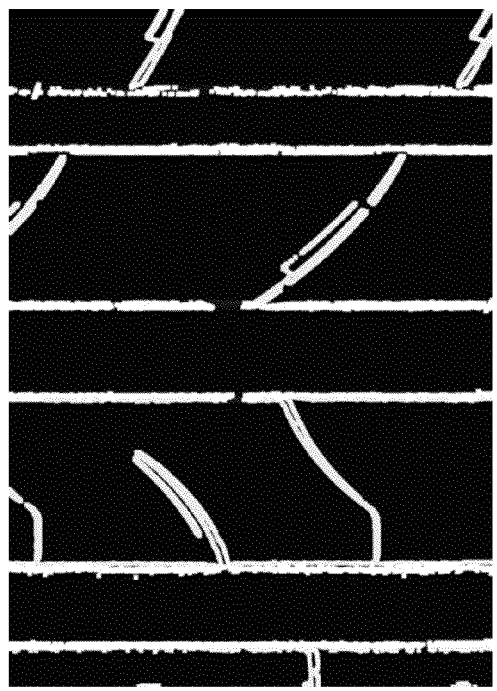
FIG. 4 represents the image of the contours of the reliefs of the exterior surface of the tyre, the image of FIG. 5 represents a view of the exterior surface after processing with the aid of the first and second transformation.

FIG. 4 illustrates the result of this operation which makes it possible for just the values of the contours of the reliefs of the surface to be made to stand out from the background of the image.

The object of the second processing is to reduce the false-measurement values in the narrow band representing the contours of the reliefs. Accordingly, each pixel of this zone is assigned the grey level value equal to the value obtained after the first transformation.

Figure 5:
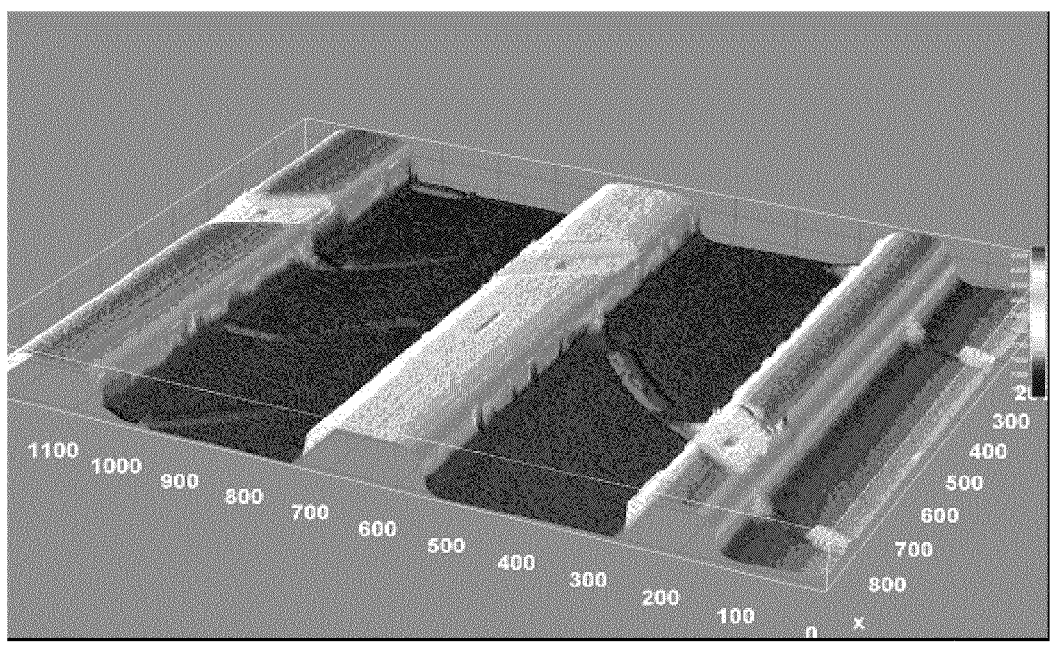

FIG. 5 makes it possible to illustrate the result obtained after the implementation of the first and second processing. It is observed that the false-measurement points have totally disappeared and are no longer liable to disturb the digital processings of the image with a view to carrying out the inspection of the compliance of the surface of the tyre.

As was indicated previously, this method applies particularly well to the zones revealing strong variations of reliefs and therefore to the external parts of the surface of the tyre. However, in a nonlimiting manner, the use of this same method to refine the images of the internal part of the tyre when they comprise relief elements such as striations is not excluded.

The invention claimed is:

1. A method for processing an image of a surface of a tyre, in which a three-dimensional digital image of the surface is captured, in which each pixel of a plurality of pixels of a plane of the image is assigned an item of information relating to an elevation of the pixel with respect to the surface, the method comprising:
   digitally processing the image by using a computer processor to:
   utilize a morphological operator that includes an opening and a closing and that uses a structuring element of given size and shape to perform a first transformation of the image of the surface so as to identify respective first-transformation grey-level values of pixels situated abnormally above or below the surface;
   determine elements of a plurality of contours of relief of the surface using a gradient-type morphological operator, and then performing a thresholding operation to extract the plurality of contours of the relief of the surface; and
   perform a second transformation of the image of the surface by assigning to each pixel of a contour a value of the plurality of contours of relief of the surface a second-transformation grey-level value equal to the first-transformation grey-level value for that pixel obtained from the first transformation;
   wherein a result of the processing of the image is used to determine where the tyre is in compliance with a reference.

2. The method according to claim 1, wherein a grey-level value of a pixel of the plurality of pixels is representative of an elevation of a corresponding point of the surface.

3. The method according to claim 1, wherein the morphological operator is a square.

4. The method according to claim 2, wherein the morphological operator is a square.

5. The method according to claim 3, wherein a width of the square of the morphological operator lies between 8 and 15 pixels.

6. The method according to claim 4, wherein a width of the square of the morphological operator lies between 8 and 15 pixels.

7. The method according to claim 1, wherein the image is that of an external surface of the tyre.

8. The method according to claim 2, wherein the image is that of an external surface of the tyre.

9. The method according to claim 3, wherein the image is that of an external surface of the tyre.

10. The method according to claim 4, wherein the image is that of an external surface of the tyre.

11. The method according to claim 5, wherein the image is that of an external surface of the tyre.

12. The method according to claim 6, wherein the image is that of an external surface of the tyre.

\* \* \* \* \*